(12) United States Patent
Dong et al.

(10) Patent No.: US 12,297,445 B2
(45) Date of Patent: May 13, 2025

(54) RECOMBINANT VECTOR CONTAINING IMMUNOGENIC PROTEIN OF AFRICAN SWINE FEVER VIRUS, RECOMBINANT BACTERIA AND USE THEREOF

(71) Applicant: CHANGSHA LVYE BIOTECHNOLOGY CO. LTD, Changsha (CN)

(72) Inventors: Wei Dong, Changsha (CN); Xiaohong Xie, Changsha (CN); Lixin Wen, Changsha (CN); Chaoliang Wu, Changsha (CN); Xin Li, Changsha (CN); Yuanyuan Zhu, Changsha (CN); Yongyong Zhang, Changsha (CN); Jiahao Huang, Changsha (CN)

(73) Assignee: CHANGSHA LVYE BIOTECHNOLOGY CO. LTD, Changsha (CN)

( * ) Notice: Subject to any disclaimer, the term of this patent is extended or adjusted under 35 U.S.C. 154(b) by 1015 days.

(21) Appl. No.: 17/299,375

(22) PCT Filed: Aug. 18, 2020

(86) PCT No.: PCT/CN2020/109703
§ 371 (c)(1),
(2) Date: Jun. 3, 2021

(87) PCT Pub. No.: WO2021/217959
PCT Pub. Date: Apr. 11, 2021

(65) Prior Publication Data
US 2022/0315947 A1    Oct. 6, 2022

(30) Foreign Application Priority Data
Apr. 26, 2020  (CN) .......... 202010339345.5

(51) Int. Cl.
| | | |
|---|---|---|
| C12N 15/86 | (2006.01) |
| A61K 35/00 | (2006.01) |
| A61K 35/747 | (2015.01) |
| A61K 39/12 | (2006.01) |
| A61P 31/20 | (2006.01) |
| C12N 1/20 | (2006.01) |

(52) U.S. Cl.
CPC ............ *C12N 15/86* (2013.01); *A61K 35/747* (2013.01); *A61K 39/12* (2013.01); *A61P 31/20* (2018.01); *C12N 1/20* (2013.01); *A61K 2035/115* (2013.01); *C12N 2710/12034* (2013.01); *C12N 2710/12043* (2013.01); *C12N 2710/12052* (2013.01); *C12N 2710/12071* (2013.01)

(58) Field of Classification Search
None
See application file for complete search history.

(56) References Cited

FOREIGN PATENT DOCUMENTS

| | | |
|---|---|---|
| CN | 103215298 A | 7/2013 |
| CN | 106188307 A | 12/2016 |
| CN | 110618279 A | 12/2019 |
| CN | 111454982 A | 7/2020 |
| WO | 2015091322 A1 | 6/2015 |

OTHER PUBLICATIONS

Deng, Yichao, et al. "Construction and expression of a recombinant plasmid containing the porcine epidemic diarrhea virus S1 gene delivered by Lactobacillus." BIBE 2019; The Third International Conference on Biological Information and Biomedical Engineering. VDE, 2019. (Year: 2019).*

Lokhandwala, Shehnaz, et al. "Induction of robust immune responses in swine by using a cocktail of adenovirus-vectored African swine fever virus antigens." Clinical and Vaccine Immunology 23.11 (2016): 888-900. (Year: 2016).*

Chen Jianghua, Chen Wenzhi, Liang Wangwang, Feng Zhihua; "The research trends in vaccine development against African swine fever virus;" Fujian Provincial Key Laboratory of Innate Immune Biology, Biomedical Research Center of South China, Fujian Normal University, Fuzhou; 2019.

Natasha N. Gaudreault, Juergen A. Richt; "Subunit Vaccine Approaches for African Swine Fever Virus;" Published Jun. 25, 2019.

* cited by examiner

*Primary Examiner* — Robert J Yamasaki
(74) *Attorney, Agent, or Firm* — Renner, Otto, Boisselle & Sklar, LLP (57) ABSTRACT

A recombinant vector containing the immunogenic protein of African swine fever virus, a recombinant bacterium and use thereof, and relates to the technical field of gene recombination. The recombinant vector can be used to construct a recombinant *Lactobacillus* expressing the immunogenic protein of African swine fever virus, and after mixing the *Lactobacillus* solution that can secrete protein p72 and protein p54, respectively, an oral live bacterial preparation for preventing African swine fever can be prepared. The oral live bacteria preparation prepared by the disclosure can safely, effectively and quickly prevent the infection of African swine fever virus to pigs, and does not contain an immune process.

4 Claims, 3 Drawing Sheets

Specification includes a Sequence Listing.

RECOMBINANT VECTOR CONTAINING IMMUNOGENIC PROTEIN OF AFRICAN SWINE FEVER VIRUS, RECOMBINANT BACTERIA AND USE THEREOF

CROSS REFERENCE TO RELATED APPLICATION

This patent application claims the benefit and priority of Chinese Patent Application No. 202010339345.5 filed on Apr. 26, 2020, the disclosure of which is incorporated by reference herein in its entirety as part of the present application.

REFERENCE TO SEQUENCE LISTING

A Sequence Listing in ASCII text format, submitted pursuant to 37 C.F.R. § 1.821, entitled 2021-05-24_Sequence-Listing_BGAO10PUS01.txt, 6 kilobytes in size, created on May 14, 2021 and filed via EFS-Web, is hereby incorporated by reference in its entirety.

TECHNICAL FIELD

The disclosure belongs to the technical field of gene recombination, and particularly relates to a recombinant vector containing immunogenic protein of African swine fever virus, a recombinant bacteria and use thereof.

BACKGROUND ART

African swine fever (ASF) is an acute, febrile and highly contagious animal infectious disease. The morbidity and mortality of ASF can reach as high as 100%, which is the number one killer in swine industry. At present, there is no commercial vaccine available. African swine fever virus (ASFV) is the only member of African swine fever virus family African swine fever virus genus, which is 175-215 nm in diameter, icosahedron symmetrical, and with capsule membrane coated on the nucleocapsid. The genome of ASFV is a double strand linear DNA with a size of 170-190 kb.

African swine fever virus can cause highly contact transmission between domestic pigs and various wild boars, mainly entering pigs through the mouth and upper respiratory system, causing infection in nasopharynx or tonsil, then spreading rapidly to mandibular lymph nodes and invading the whole body through lymph and blood.

Since there is no commercial vaccine against ASFV on the market, the safest, most economical and effective prevention and control method is biosafety prevention and control method, the principle of which is to block the contact between virus and organism. However, none of the existing methods can guarantee that the virus will no longer come into contact with the body.

SUMMARY

In view of this, the purpose of the present disclosure is to provide a recombinant vector containing the immunogenic protein of African swine fever virus, a recombinant bacteria and use thereof, to construct a *Lactobacillus* expression system expressing p72 and p54 proteins of African swine fever virus, and to provide a theoretical basis for the development of a mucosal infection blocking oral agent for blocking virus infection.

In order to achieve the above purpose of the disclosure, the present disclosure provides the following technical solution:

The present disclosure provides a recombinant vector containing immunogenic protein of African swine fever virus, wherein the recombinant vector takes *Lactobacillus* expression vector pVE5523 as basic vector, and the nucleotide sequence encoding the immunogenic protein of African swine fever virus is cloned between EcoRV and SalI restriction sites of the basic vector.

In some embodiments, the immunogenic protein of African swine fever virus comprises p72 protein and p54 protein of African swine fever virus of Jilin strain in China. The nucleotide sequence encoding the p72 protein of the African swine fever virus of Jilin strain in China is set forth in SEQ ID NO:1, and the nucleotide sequence encoding the p54 protein of the African swine fever virus of Jilin strain in China is set forth in SEQ ID NO:2.

The present disclosure provides a recombinant *Lactobacillus* expressing the immunogenic protein of African swine fever virus, wherein the recombinant *Lactobacillus* comprises the above recombinant vector.

The present disclosure also provides a constructing method of the recombinant *Lactobacillus*, wherein comprising:

(1) respectively cloning the nucleotide sequence encoding the p72 protein of African swine fever virus and the nucleotide sequence encoding the p54 protein of African swine fever virus into the pVE5523 *Lactobacillus* expression vector to construct recombinant plasmids pVE5523-ASFV-p72 and pVE5523-ASFV-p54;

(2) respectively transforming the recombinant plasmids pVE5523-ASFV-p72 and pVE5523-ASFV-p54 into *Lactobacillus* competent cells to obtain recombinant *Lactobacillus* expressing p72 protein of African swine fever virus and recombinant *Lactobacillus* expressing p54 protein of African swine fever virus.

The present disclosure also provides an oral live bacteria preparation for preventing African swine fever infection, wherein the active ingredients of the oral live bacteria preparation comprise recombinant *Lactobacillus* expressing p72 protein of African swine fever virus and recombinant *Lactobacillus* expressing p54 protein of African swine fever virus constructing by the above constructing method.

In some embodiments, the live bacteria ratio of the recombinant *Lactobacillus* expressing p72 protein of African swine fever virus to the recombinant *Lactobacillus* expressing p54 protein of African swine fever virus is $(0.8–1.2) \times 10^8$ cfu: $(0.8–1.2) \times 10^8$ cfu.

The disclosure provides a recombinant vector containing immunogenic protein of African swine fever virus, which can be used to construct recombinant *Lactobacillus* expressing immunogenic protein of African swine fever virus, and after mixing the recombinant *Lactobacillus* expressing African swine fever virus antigen proteins p72 and p54, an oral live bacteria preparation for preventing African swine fever virus infection is prepared. In the present disclosure, after pigs take the preparation, the antigen protein (the mixture of protein p72 and p54) secreted by *Lactobacillus* in the preparation adheres to the mucous membrane on the surface of organism cells, and forms an antigen protein biofilm on the mucous membrane surface. The antigen protein can be combined with the virus binding site on the target cells to seal the virus receptor protein site on the mucous membrane surface, thus playing the role of ecological occupation. When the live viruses in the environment invade the body, the virus binding site on the target cell has been completely blocked by antigen protein biofilm, and the virus can not bind to the virus binding site on the target cell, thus effectively blocking the combination of the virus with the receptor on the cell surface and preventing African swine fever.

Compared with vaccines, the oral preparation prepared by the disclosure is safer, more effective and faster. The safety of the oral preparation disclosed by the disclosure is manifested in that the effective components only secrete viral functional proteins, no viral genes exist, and no virus variation can be caused. The effectiveness is manifested in that the effective components of the oral preparation only secrete protective antigens, act on the mucosal site on the body surface, and cover the mucosal surface where the target cells of African swine fever virus are located. When the virus invades, the binding site between antigen protein and mucosal surface cells is blocked and sealed, thus blocking the virus infection path. The rapidity is manifested in that the secreted protein expressed by *Lactobacillus* directly preempts the receptor that the virus binds to the target cell, thus blocking the virus infection, and no immune response process is needed.

DETAILED DESCRIPTION OF THE EMBODIMENTS

The disclosure will be further explained with embodiments below.

The present disclosure provides a recombinant vector containing immunogenic protein of African swine fever virus, wherein the recombinant vector takes *Lactobacillus* expression vector pVE5523 as basic vector, and the nucleotide sequence encoding the immunogenic protein of African swine fever virus is cloned between EcoRV and SalI restriction sites of the basic vector.

Figure 1:
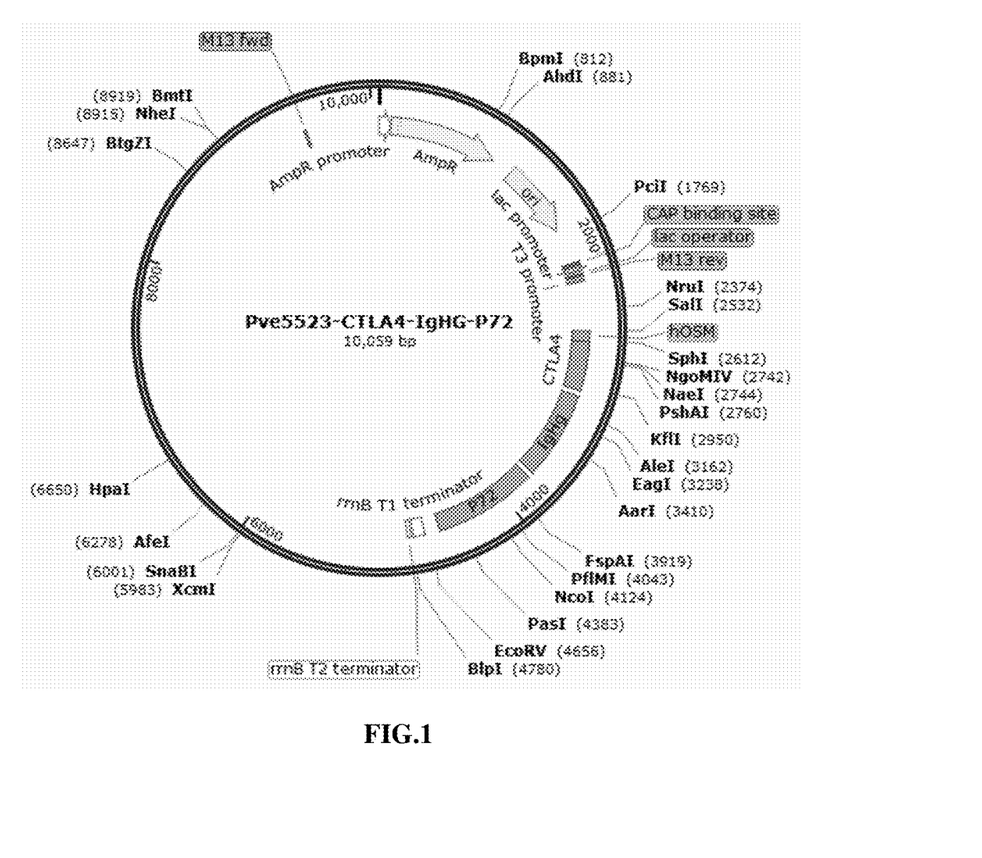
FIG. 1 is a plasmid structure diagram of the recombinant vector pVE5523-ASFV-p72 in the present disclosure.
Figure 2:
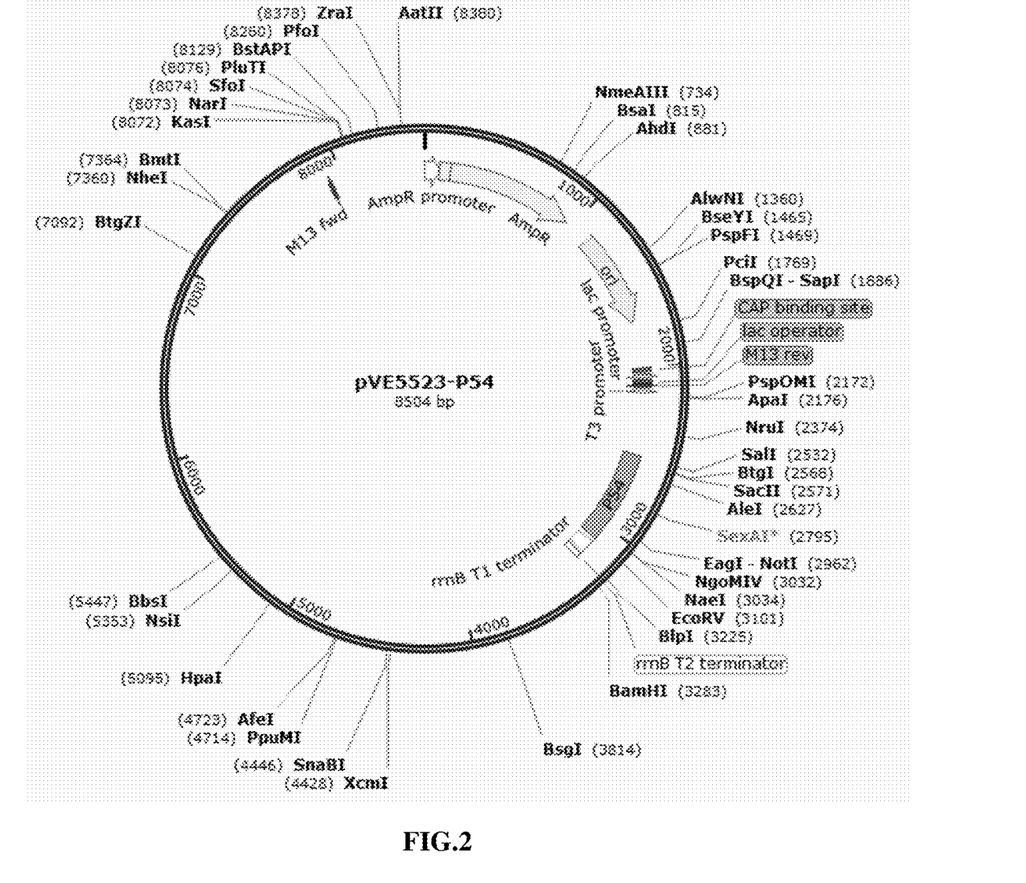
FIG. 2 is a plasmid structure diagram of the recombinant vector pVE5523-ASFV-p54 in the present disclosure.

The immunogenic protein of African swine fever virus comprises p72 protein and p54 protein of African swine fever virus of Jilin strain in China. The nucleotide sequence encoding the p72 protein of the African swine fever virus of Jilin strain in China is set forth in SEQ ID NO:1, and the nucleotide sequence encoding the p54 protein of the African swine fever virus of Jilin strain in China is set forth in SEQ ID NO:2. The nucleotide sequence set forth in SEQ ID NO:1 is cloned between the EcoRV and SalI restriction sites of the basic vector to form a recombinant vector pVE5523-ASFV-p72, and the structure of the recombinant plasmid is shown in FIG. 1. The nucleotide sequence set forth in SEQ ID NO:2 is cloned between the EcoRV and SalI restriction sites of the basic vector to form a recombinant vector pVE5523-ASFV-p54, and the structure of the recombinant plasmid is shown in FIG. 2. The present invention has no special limitation on the constructing method of the recombinant vector, and the conventional constructing method of the recombinant vector will do.

The present disclosure provides a recombinant *Lactobacillus* expressing the immunogenic protein of African swine fever virus, wherein the recombinant *Lactobacillus* comprises the above recombinant vector.

The present disclosure also provides a constructing method of the recombinant *Lactobacillus*, wherein comprising:
(1) respectively cloning the nucleotide sequence encoding the p72 protein of African swine fever virus and the nucleotide sequence encoding the p54 protein of African swine fever virus into the pVE5523 *Lactobacillus* expression vector to construct recombinant plasmids pVE5523-ASFV-p72 and pVE5523-ASFV-p54;
(2) respectively transforming the recombinant plasmids pVE5523-ASFV-p72 and pVE5523-ASFV-p54 into *Lactobacillus* competent cells to obtain recombinant *Lactobacillus* expressing p72 protein of African swine fever virus and recombinant *Lactobacillus* expressing p54 protein of African swine fever virus.

Before performing the cloning step, the p72 and p54 gene sequences of African swine fever virus of Jilin strain in China searched in GenBank are preferably optimized to form sequences set forth in SEQ ID NO:1 and SEQ ID NO:2, and then the cloning is performed.

When the cloning is performed, the vector pVE5523 is preferably digested with SalI/EcoRV, and the sequences set forth in SEQ ID NO:1 and SEQ ID NO:2 are digested with the same enzyme. After ligating the above digested fragments, the recombinant plasmids pVE5523-ASFV-p72 and pVE5523-ASFV-p54 shown in FIG. 1 and FIG. 2 are formed.

In the disclosure, the recombinant plasmids are used for transforming the ATCC393 *Lactobacillus casei* competent cells by electrotransformation to obtain the recombinant *Lactobacillus*. After obtaining the recombinant *Lactobacillus*, the recombinant *Lactobacillus* are preferably amplified in MRS liquid medium, and the recombinant plasmid is extracted for fluorescence quantitative PCR detection. The primers and amplified sequences used for fluorescence quantitative PCR detection in this disclosure are as follows:

Detection of p72 fluorescence quantitative PCR:

```
P72 forward primer (SEQ ID NO: 3):
AGTTCGGATGTCACAACGCTTG;

P72 reverse primer (SEQ ID NO: 4):
TTTGCTTTGGTGCGGCTTGT;

P72 amplified sequence (SEQ ID NO: 5):
AGTTCGGATGTCACAACGCTTGTGCGCAAATTTT

GCATCCCAGGGGATAAAATGACTGGATATAAGCA

CTTGGTTGGCCAGGAGGTATCGGTGGAGGGAACC

AGTGGCCCTCTCCTATGCAACATTCATGATTTGC

ACAAGCCGCACCAAAGCAAA;
```

P54 fluorescence quantitative PCR:

```
P54 forward primer (SEQ ID NO: 6):
AGCCACTCCACAACCAGGTAC;

P54 reverse primer (SEQ ID NO: 7):
GCCCTCCAGTTGCCATGATTAG;

P54 amplified sequence (SEQ ID NO: 8):
AGCCACTCCACAACCAGGTACCTCTAAACCGGCTGG

AGCCACTACAGGCAACGTAGGCAAGCCAATTACAGA

CAGGCCAGTTGCCATGAATAGGCCAGTTACGAACAG

CTCGGTCGCGGACAGGCCAGTTATGAACAACCCAGT

TACGGACAGACTAATCATGGCAACTGGAGGGC.
```

The recombinant *Lactobacillus* prepared by the constructing method can secrete recombinant immunogenic proteins p72 and p54 of African swine fever virus respectively according to different recombinant plasmids.

The present disclosure also provides an oral live bacteria preparation for preventing African swine fever infection, wherein the active ingredients of the oral live bacteria preparation comprise recombinant *Lactobacillus* expressing p72 protein of African swine fever virus and recombinant *Lactobacillus* expressing p54 protein of African swine fever virus constructed by the above constructing method.

In the oral live bacteria preparation, the live bacteria ratio of the recombinant *Lactobacillus* expressing p72 protein of African swine fever virus to the recombinant *Lactobacillus* expressing p54 protein of African swine fever virus is $(0.8\text{-}1.2)\times 10^8$ cfu: $(0.8\text{-}1.2)\times 10^8$ cfu, more preferably $1\times 10^8$ cfu.

In the following, the recombinant vector containing the immunogenic protein of African swine fever virus, recombinant bacteria and use thereof provided by the present disclosure will be described in detail with reference to the Examples, but they should not be understood as limiting the scope of protection of the present disclosure.

EXAMPLE 1

Acquisition of p72 and p54 Gene Sequences of African Swine Fever Virus p54 protein of African swine fever virus exists in the inner capsule of virus particles, which is one of the main structural proteins and strong immunogenic proteins of ASFV, and participates in the adsorption and entry of virus to target cells. The p72 and p54 gene sequences (P72: GenBank: MK189456.1; P54: GenBank: MK214679.1) of African swine fever virus of Jilin strain in China in GenBank were optimized and modified, then synthesized by Nanjing Genescript Biotechnology Co., Ltd, and the base sequences were set forth in SEQ ID NO:1 and SEQ ID NO:2.

EXAMPLE 2

Acquisition of Recombinant Expression Vectors pVE5523-ASFV-p72 and pVE5523-ASFV-p54
1 Materials and Methods
1.1 Materials and Sources The restriction enzymes SalI and EcoRV were all purchased from NEB company, and Taq enzyme, dNTP, DNA Marker DL2000, DL15000, Agarose Gel DNA Purification Kit and Mini BEST Plasmid purification kit were purchased from Dalian Takara company, and the cloning vector pVE5523 was provided by Nanjing Genescript Biotechnology Co., Ltd.
1.2 Testing Method The fragments of cloning vector pVE5523 digested by SalI/EcoRV were ligated with fragments of p72 and p54 gene digested by the same SalI/EcoRV enzyme, after the electrotransformation, the recombinant plasmid was extracted and sent to Nanjing Genescript Biotechnology Co., Ltd for sequencing verification.
2 Testing Results Sequencing results of recombinant plasmid: the recombinant plasmid after gene sequencing was compared with the inserted p72 and p54 gene fragments, and the sequencing results were consistent with expectations, indicating that the synthesized p72 and p54 gene fragments were successfully inserted into *Lactobacillus* vector pVE5523, and the recombinant plasmid was successfully constructed, the positive plasmids were named pVE5523-ASFV-p72 and pVE5523-ASFV-p54 respectively.

EXAMPLE 3

Preparation and Detection of p72 and p54 Genes Expressing African Swine Fever Virus
1 Materials and Methods
1.1 Materials and Sources Erythromycin (Emr) was purchased from Biodee Biotechnology Co., Ltd.
1.2 Testing Method Electrotransformation of target genes in *Lactobacillus* ATCC393 and screening of resistant strains: the electrotransformed *Lactobacillus* ATCC393 was spread on MRS solid culture plate containing 5 µg/ml erythromycin, the plate was cultured in incubator at 30° C. for 72 hours, and the colonies on the plate were selected and inoculated into MRS liquid culture medium containing 5 µg/ml erythromycin, and cultured at 30° C. for 72 hours. The plasmids in bacteria were extracted and identified by fluorescence quantitative PCR. The identified primers and amplified sequences are as follows:

Detection of p72 fluorescence quantitative PCR:

```
P72 forward primer (SEQ ID NO: 3):
AGTTCGGATGTCACAACGCTTG;

P72 reverse primer (SEQ ID NO: 4):
TTTGCTTTGGTGCGGCTTGT;

P72 amplified sequence (SEQ ID NO: 5):
AGTTCGGATGTCACAACGCTTGTGCGCAAATTTTG

CATCCCAGGGGATAAAATGACTGGATATAAGCACT

TGGTTGGCCAGGAGGTATCGGTGGAGGGAACCAGT

GGCCCTCTCCTATGCAACATTCATGATTTGCACAA

GCCGCACCAAAGCAAA;
```

P54 fluorescence quantitative PCR:

```
P54 forward primer (SEQ ID NO: 6):
AGCCACTCCACAACCAGGTAC;

P54 reverse primer (SEQ ID NO: 7):
GCCCTCCAGTTGCCATGATTAG;

P54 amplified sequence (SEQ ID NO: 8):
AGCCACTCCACAACCAGGTACCTCTAAACCGGCTGG

AGCCACTACAGGCAACGTAGGCAAGCCAATTACAGA

CAGGCCAGTTGCCATGAATAGGCCAGTTACGAACAG

CTCGGTCGCGGACAGGCCAGTTATGAACAACCCAGT

TACGGACAGACTAATCATGGCAACTGGAGGGC.
```

2 Testing Results

Figure 3:
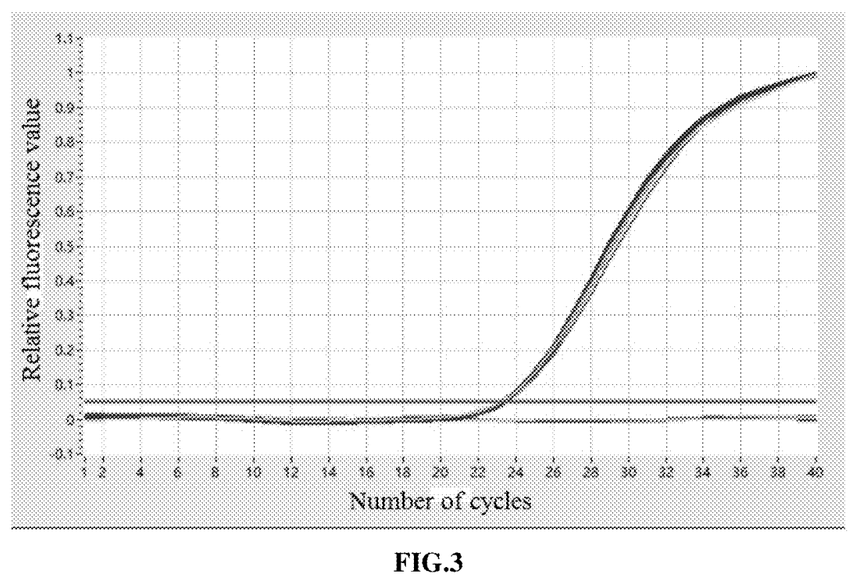
FIG. 3 is an amplification curve for verifying p72 expression in the present disclosure.
Figure 4:
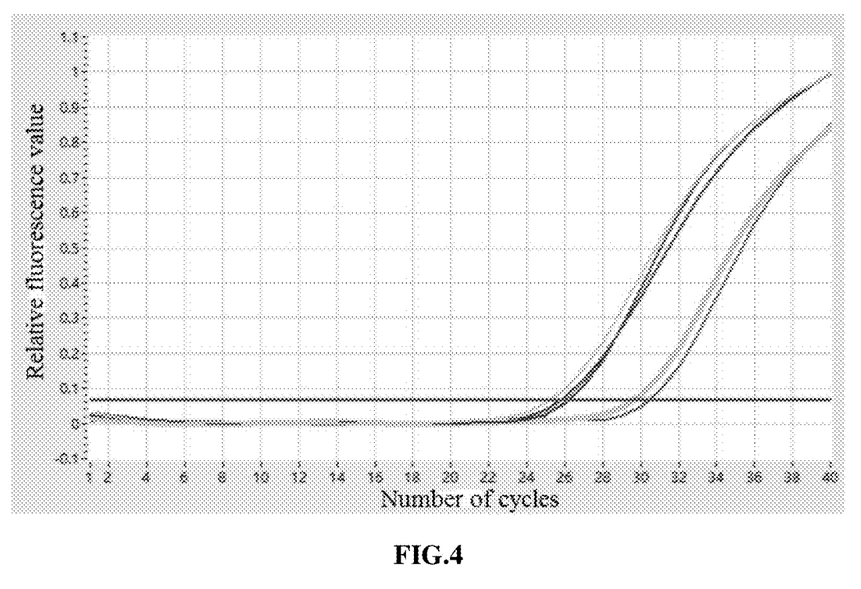
FIG. 4 is an amplification curve for verifying p54 expression in the present disclosure.

The amplified recombinant plasmids were detected by fluorescence quantitative PCR, and the amplification curves are shown in FIG. 3 and FIG. 4 respectively. The positive recombinant plasmids have typical amplification curve with CT values ranging from 19 to 22, while ATCC393 competent control has no amplification curve, indicating that the recombinant plasmids pVE5523-ASFV-p54 and pVE5523-ASFV-p72 have been successfully transformed into ATCC393 competent cells.

EXAMPLE 4

Method for Culturing Recombinant *Lactobacillus* Expression System

The recombinant *Lactobacillus* expression system was inoculated into *Lactobacillus* MRS liquid culture medium with 1% inoculation amount, and the fermentation broth was obtained at 35° C. for 72 hours.

Viable Bacteria Count of Recombinant *Lactobacillus*

With flat surface dispersion method:
1. Numbering: 9 sets of sterile MRS solid agar culture plates were marked as $10^{-4}$, $10^{-5}$ and $10^{-6}$ (3 sets for each dilution) with a marker respectively. Another 6 test tubes containing 4.5 mL sterile water were taken and marked as $10^{-1}$, $10^{-2}$, $10^{-3}$, $10^{-4}$, $10^{-5}$ and $10^{-6}$ in turn.
2. Diluting: 0.5 ml of *Lactobacillus* suspension (sample to be tested) that well mixed was suck to the $10^{-1}$ test tube with a 1 mL pipette, which was a 10 times diluent. The $10^{-1}$ test tube was placed on the test tube oscillator for oscillation, to make the bacterial liquid mixed evenly. Another 1ml pipette was used to insert into the $10^{-1}$ test tube to blow and suck the bacterial suspension back and forth for three times, to further disperse and mix the bacteria. 0.5 ml bacterial liquid in the $10^{-1}$ test tube was suck to the the $10^{-2}$ test tube with the pipette used in the previous step, obtaining a 100 times diluent, and the rest can be deduced by analogy.
3. Sampling and coating: 0.2 ml of diluted bacterial suspensions were taken from $10^{-4}$, $10^{-5}$ and $10^{-6}$ test tubes respectively, and put into the corresponding numbered sterile agar medium plate, the bacterial solution was uniformly dispersed in the agar medium with a sterile glass coating rod, and the bacteria was cultivated in a constant temperature incubator at 37° C.
4. Accounting: After culturing for 48 hours, the agar medium plate was taken out for counting the colonies, and the average number of colonies on three plates with the same dilution was calculated, the calculating formula was as follows:

Colony forming unit per milliliter (cfu)=the average number of colonies repeated three times with the same dilution×dilution times×5.

EXAMPLE 5

The *Lactobacillus* that can secrete recombinant p72 and p54 proteins prepared in Example 4 was diluted into 0.8-1.2×$10^8$ cfu/ml bacterial liquid and mixed in the ratio of 1:1. The mixed bacterial solution was administered to SPF New Zealand rabbits and SD rats in the form of oral liquid. Meanwhile, the negative control group A was given the same volume of normal saline and the control group B was given the same volume of MRS culture solution. Four New Zealand rabbits and SD rats in each group were observed for 2 weeks, and no abnormal phenomena such as abnormal body temperature and allergy occurred in 24 animals. Therefore, the *Lactobacillus* that can secrete recombinant p72 and p54 protein prepared by the disclosure is safe and has no side effect.

EXAMPLE 6

There were about 300 pigs in a farm in Taihu County, Anhui Province, with sizes ranging from 20 kg to 100 kg, which were divided into three breeding areas, some pigs in the second breeding areas had become ill and died one after another. On Jan. 23, 2020, the test of recombinant *Lactobacillus* preparation was carried out in this farm, the test lasted for 21 days and was divided into three groups, the pigs were given orally at a dose of 5 ml/head. The control group was set in the first breeding area with 112 pigs in total, the test group was set in the second and third breeding area. Before the experiment, the pigs in the first and third breeding area were in a healthy state, and the second breeding area was in an outbreak state of African swine fever before the test was carried out on January 23.

The testing results are shown in Table 1, wherein the number of pigs in the control group ranged from 112 to 66, and 46 pigs died, with a mortality rate of 41.07%. Because the second breeding area was in the disease stage before the experiment, the number decreased from 45 to 28 after using the recombinant *Lactobacillus* preparation, and 17 died, with a mortality rate of 37.78%. One pig died during the test in the third breeding area, with a mortality rate of 1.08%. In the whole test stage, 18 pigs died in the test group (the second and third breeding areas), with a mortality rate of 13.04%. The results showed that the recombinant *Lactobacillus* preparation had good effect.

TABLE 1

Comparison of testing results of recombinant *Lactobacillus*

| | Control group | Test group | |
|---|---|---|---|
| Time/Group | Breeding area 1 | Breeding area 2 | Breeding area 3 |
| January 23-February 13 | The number of pigs in the control group ranged from 112 to 66, and 46 pigs died | The second breeding area was in the disease stage before the experiment, the number decreased from 45 to 28 after using the recombinant *Lactobacillus* preparation, and 17 died | The number of pigs ranged from 93 to 92, and one pig died |
| Mortality rate | 41.07% | | 13.04% |

EXAMPLE 7

An African swine fever epidemic occurred in a farm in Yiyang City, Hunan Province in 2019, more than 400 fattening pigs were treated harmlessly and the farm was completely disinfected. In April 2020, a total of 120 nursing pigs and fattening pigs were introduced, and 402 pigs were introduced on May 27, the pathogen detection of African swine fever was not conducted before the introduction. Among the pigs introduced in April, some pigs suffered from non-eating, poor mental state and the like, and 1 pig died. Then 40 pigs were randomly sampled to detect pathogen of African swine fever, and 2 nursing pigs were suspected of African swine fever, and farmers immediately isolated the suspected pigs and strengthen the biosafety measures of the farm, two suspected pigs died within a week, and then died one after another. On May 21st, 500 ml of the recombinant *Lactobacillus* preparation prepared in Example 4 was dissolved in 30 kg of water, and mixed with 25 kg of feed (feeding amount of 100 pigs per day), and fed twice a day, 2-3 times a week. After the product being used, the overall health status of pigs improved obviously, and no death occurred.

TABLE 2

Collection table of pig farm use effect of recombinant *Lactobacillus* products

| | Introduction information | Before using the product | After the product is used |
|---|---|---|---|
| 5# Building | On Apr. 1, 2020, 60 pigs were introduced | Since April 13, deaths occurred one after another, with 9 deaths. | The health status of pigs improved obviously, and no death happened |
| 9# Building | On Apr. 1, 2020, 60 pigs were introduced | Since April 19, deaths occurred one after another, with 18 deaths. | The health status of pigs improved obviously, and no death happened |

All the 402 pigs introduced in May grew well using the scheme of Example 4, and no pigs were infected.

EXAMPLE 8

A pig farm in Jinhua City, Zhejiang Province, was non-pestilence positive in November 2019. At present, there were 380 sows and about 3,900 fattening pigs in stock. All sows and fattening pigs were administrated with the recombinant *Lactobacillus* products prepared in Example 4. From the beginning of the year to May, 10 ml per pig was taken orally, once every 3 days. From May 17, 500 ml of the recombinant *Lactobacillus* preparation prepared in Example 4 was dissolved in 30 kg of water, and mixed with 25 kg of feed (feeding amount of 100 pigs per day), and fed twice a day, 2-3 times a week. After the Spring Festival in 2020, there was an outbreak of non-plague in Wucheng District, Jinhua, and by August 10th, everything in the pig farm was normal.

The above are only the preferred embodiments of the present disclosure. It should be pointed out that for those of ordinary skill in the art, without departing from the principle of the present disclosure, several improvements and modifications can be made, and these improvements and modifications should also be regarded as the protection scope of the present disclosure.

What is claimed is:

1. An oral live bacteria preparation for preventing African swine fever infection, wherein the active ingredients of the oral live bacteria preparation comprise recombinant *Lactobacillus* expressing p72 protein of African swine fever virus and recombinant *Lactobacillus* expressing p54 protein of African swine fever virus;
    wherein the recombinant *Lactobacillus* expressing p72 protein of African swine fever virus comprises a first recombinant vector containing a *Lactobacillus* expression vector pVE5523 with a nucleotide sequence encoding the p72 protein of African swine fever virus cloned between EcoRV and SaI restriction sites of the first recombinant vector, and the recombinant *Lactobacillus* expressing p54 protein of African swine fever virus comprises a second recombinant vector containing a *Lactobacillus* expression vector pVE5523 with a nucleotide sequence encoding the p54 protein of African swine fever virus cloned between EcoRV and SaII restriction sites of the second recombinant vector; and wherein upon administration of the preparation to a subject, the *Lactobacillus* secrete p54 and p72 antigen proteins capable of forming a biofilm on a mucus membrane of the subject that blocks binding of African swine fever virus.

2. The oral live bacteria preparation according to claim 1, wherein an amount of the recombinant *Lactobacillus* expressing p72 protein of African swine fever virus is $0.8\text{-}1.2\times10^8$ cfu; and an amount of the recombinant *Lactobacillus* expressing p54 protein of African swine fever virus is $0.8\text{-}1.2\times10^8$ cfu.

3. The oral live bacteria preparation according to claim 2, wherein the amount of the recombinant *Lactobacillus* expressing p72 protein of African swine fever virus is $1\times10^8$ cfu; and the amount of the recombinant *Lactobacillus* expressing p54 protein of African swine fever virus is $1\times10^8$ cfu.

4. A method for treating African swine fever, wherein the method comprises: allowing animals to ingest the oral live bacteria preparation according to claim 1.

\* \* \* \* \*

SEQUENCE LISTING

```
<160> NUMBER OF SEQ ID NOS: 8

<210> SEQ ID NO 1
<211> LENGTH: 2128
<212> TYPE: DNA
<213> ORGANISM: Artificial Sequence
<220> FEATURE:
<223> OTHER INFORMATION: The nucleotide sequence encoding the p72
      protein of the African swine fever virus of Jilin strain in China

<400> SEQUENCE: 1
gtcgacatgg gtgtactgct cacacagagg acgctgctca gtctggtcct tgcactcctg      60
tttccaagca tggcgagcat gcatatgaaa gggatgcacg tggcccaacc tgcagtagtg     120
ctggccaaca gccggggtgt tgccagcttt gtgtgtgagt atgggtctgc aggcaaagct     180
gccgaggtcc gggtgacagt gctgcggcgg gccggcagcc agatgactga agtctgtgcc     240
gcgacatata ctgtggagga tgagttgacc ttccttgatg actctacatg cactggcacc     300
tccaccgaaa acaaagtgaa cctcaccatc caagggctga gagccgtgga cactgggctc     360
tacatctgca aggtggagct cctgtaccca ccaccctact atgtgggtat gggcaacggg     420
acccagattt atgtcattga tccagaacca tgcccagatt ctgatggtgg cggtggctcg     480
ggcggtggtg gatctggtgg cggcggatct acaaagacca aaccaccatc ccccatatcg     540
ccaggctccg aagtggccgg gtcctcggtc ttcatcttcc ctccaaaacc caaggacacc     600
ctcatgatct cccagacccc cgaggtcacg tgcgtggtgg tggacgtcag caaggagcac     660
gccgaggtcc agttctcctg gtacgtggac ggcgtagagg tgcacacggc cgagacgaga     720
ccaaaggagg agcagttcaa cagcacctac cgtgtggtca gcgtcctgcc catccagcac     780
caggactggc tgaaggggaa ggagttcaag tgcaaggtca acaacgtaga cctcccagcc     840
cccatcacga ggaccatctc caaggctata gggcagagcc gggagccgca ggtgtacacc     900 ctgccccac ccgccgagga gctgtccagg agcaaagtca ccgtaacctg cctggtcatt     960
ggcttctacc cacctgacat ccatgttgag tggaagagca acggacagcc ggagccagag    1020
ggcaattacc gcaccacccc gccccagcag gacgtggacg ggaccttctt cctgtacagc    1080
aagctcgcgg tggacaaggc aagatgggat catggagaaa catttgagtg tgcggtgatg    1140
```

```
cacgaggctc tgcacaacca ctacacccag aagtccatct ccaagactca gggtaaacct    1200
cctccatacc agcctctcgg cggcggcggc agcgaattcg gatcccatat ggacaagatt    1260
atattggccc aagacttgct gaatagcagg atctctaaca ttaaaaatgt gaacaaaagt    1320
tatgggaaac ccgatcccga acccactttg agtcaaatcg aagaaacaca tttggtgcat    1380
tttaatgcgc attttaagcc ttatgttcca gtagggtttg aatacaataa agtacgcccg    1440
catacgggta cccccacctt gggaaacaag cttacctttg gtattcccca gtacggagac    1500
tttttccatg atatggtggg ccatcatata ttgggtgcat gtcattcatc ctggcaggat    1560
gctccgattc agggcacgtc ccagatgggg gccatgggc agcttcaaac gtttcctcgc     1620
aacggatatg actgggacaa ccaaacaccc ttagagggcg ccgtttacac gcttgtagat    1680
ccttttggaa gacccattgt acccggcaca agaatgcgt accgaaactt ggtttactac     1740
tgcgaatacc ccggagaacg actttatgaa aacgtaagat tcgatgtaaa tggaaattcc    1800
ctagacgaat atagttcgga tgtcacaacg cttgtgcgca aattttgcat cccaggggat    1860
aaaatgactg atataagca cttggttggc caggaggtat cggtggaggg aaccagtggc     1920
cctctcctat gcaacattca tgatttgcac aagccgcacc aaagcaaacc tattcttacc    1980
gatgaaaatg atacgcagcg aacgtgtagc cataccaacc cgaaatttct ttcacagcat    2040
tttcccgaga actctcacaa tatccaaaca gcaggtaaac aagatattac tcctatcacg    2100
gacgcaacgt atctggacat aagatatc                                      2128

<210> SEQ ID NO 2
<211> LENGTH: 574
<212> TYPE: DNA
<213> ORGANISM: Artificial Sequence
<220> FEATURE:
<223> OTHER INFORMATION: The nucleotide sequence encoding the p54
      protein of the African swine fever virus of Jilin strain in China

<400> SEQUENCE: 2
gtcgacatgg attctgaatt ttttcaaccc gtttatccgc ggcattatgg cgaatgtttg      60
tcaccaacct ctacaccgag cttcttctcc acacatatgt gtactattct cgttgctatc     120
gtggtcttaa tcattattat catcgttcta atttatctgt tttcttcaag aaagaaaaaa     180
gctgctgccc ccgctattga ggaggaagat atacagttta taaatcctta tcaagatcag     240
cagtgggcag gagccactcc acaaccaggt acctctaaac cggctggagc cactacaggc     300
aacgtaggca agccaattac agacaggcca gttgccatga ataggccagt tacgaacagc     360
tcggtcgcgg acaggccagt tatgaacaac ccagttacgg acagactaat catggcaact     420
ggagggccag cggccgcaag tgctccttcg gatgagcttt atacaacagc cactactcag     480
aacactgctt cacaaacaat gccggctgtt gaagctctac ggcaaagaag cacctataca     540
cacaaagacc tggaaaactc cttgtaagat atca                                574

<210> SEQ ID NO 3
<211> LENGTH: 22
<212> TYPE: DNA
<213> ORGANISM: Artificial Sequence
<220> FEATURE:
<223> OTHER INFORMATION: p72 forward primer

<400> SEQUENCE: 3
agttcggatg tcacaacgct tg                                              22

<210> SEQ ID NO 4
```

```
<211> LENGTH: 20
<212> TYPE: DNA
<213> ORGANISM: Artificial Sequence
<220> FEATURE:
<223> OTHER INFORMATION: p72 reverse primer

<400> SEQUENCE: 4
tttgctttgg tgcggcttgt                                               20

<210> SEQ ID NO 5
<211> LENGTH: 156
<212> TYPE: DNA
<213> ORGANISM: Artificial Sequence
<220> FEATURE:
<223> OTHER INFORMATION: P72 amplified sequence

<400> SEQUENCE: 5
agttcggatg tcacaacgct tgtgcgcaaa ttttgcatcc caggggataa aatgactgga   60
tataagcact tggttggcca ggaggtatcg gtggagggaa ccagtggccc tctcctatgc  120
aacattcatg atttgcacaa gccgcaccaa agcaaa                            156

<210> SEQ ID NO 6
<211> LENGTH: 21
<212> TYPE: DNA
<213> ORGANISM: Artificial Sequence
<220> FEATURE:
<223> OTHER INFORMATION: P54 forward primer

<400> SEQUENCE: 6
agccactcca caaccaggta c                                             21

<210> SEQ ID NO 7
<211> LENGTH: 22
<212> TYPE: DNA
<213> ORGANISM: Artificial Sequence
<220> FEATURE:
<223> OTHER INFORMATION: P54 reverse primer

<400> SEQUENCE: 7
gccctccagt tgccatgatt ag                                            22

<210> SEQ ID NO 8
<211> LENGTH: 176
<212> TYPE: DNA
<213> ORGANISM: Artificial Sequence
<220> FEATURE:
<223> OTHER INFORMATION: P54 amplified sequence

<400> SEQUENCE: 8
agccactcca caaccaggta cctctaaacc ggctggagcc actacaggca acgtaggcaa   60
gccaattaca gacaggccag ttgccatgaa taggccagtt acgaacagct cggtcgcgga  120
caggccagtt atgaacaacc cagttacgga cagactaatc atggcaactg gagggc      176
```